(12) United States Patent
Bales

(10) Patent No.: US 12,150,684 B2
(45) Date of Patent: Nov. 26, 2024

(54) BLUNT TIP BONE SCREW

(71) Applicant: DePuy Synthes Products, Inc., Raynham, MA (US)

(72) Inventor: Joel Patrick Bales, Parkesburg, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 550 days.

(21) Appl. No.: 17/313,110

(22) Filed: May 6, 2021

(65) Prior Publication Data

US 2021/0259754 A1 Aug. 26, 2021

Related U.S. Application Data

(62) Division of application No. 14/926,153, filed on Oct. 29, 2015, now abandoned.
(Continued)

(51) Int. Cl.
*A61B 17/86* (2006.01)
*F16B 25/00* (2006.01)
*F16B 25/10* (2006.01)

(52) U.S. Cl.
CPC ...... *A61B 17/8635* (2013.01); *A61B 17/8615* (2013.01); *A61B 17/8625* (2013.01); *A61B 17/863* (2013.01); *A61B 17/864* (2013.01); *F16B 25/0084* (2013.01); *F16B 25/103* (2013.01); *F16B 25/0057* (2013.01)

(58) Field of Classification Search
CPC ... A61B 17/84; A61B 17/8625; A61B 17/863; A61B 17/8635; A61B 17/864
See application file for complete search history.

(56) References Cited

U.S. PATENT DOCUMENTS 180,554 A 8/1876 Cubberley
3,463,045 A 8/1969 Prescott
(Continued)

FOREIGN PATENT DOCUMENTS

CN 201176994 Y 1/2009
CN 107906104 A 4/2018
(Continued)

OTHER PUBLICATIONS

Biomet Microfixation, Sternalock Blu Minimally Invasive Closure Brochure, 7 pages, 2012.
(Continued)

*Primary Examiner* — Si Ming Ku
(74) *Attorney, Agent, or Firm* — BakerHostetler

(57) ABSTRACT

In one embodiment, a bone screw includes a shaft having a proximal shaft end and a distal shaft end spaced from the proximal shaft end in a distal direction along a central axis. The shaft is helically threaded between the proximal and distal shaft ends. A tip extends from the distal shaft end in the distal direction, and defines a plurality of lands with cutting flutes disposed between adjacent lands. Each land has a bore-cutting edge that extends from an inner cutting edge end to an outer cutting edge end. The inner cutting edge end is disposed at a center of the distal end of the tip, and the outer cutting edge end is spaced from the center of the distal end of the tip. The bore-cutting edges may blunt the feel of the tip so as to reduce the likelihood of soft-tissue damage.

25 Claims, 4 Drawing Sheets

Related U.S. Application Data

(60) Provisional application No. 62/075,021, filed on Nov. 4, 2014.

(56) References Cited

U.S. PATENT DOCUMENTS

| | | | |
|---|---|---|---|
| 4,016,795 | A | 4/1977 | Gill |
| 4,016,975 | A | 4/1977 | Hammer |
| 4,537,185 | A | 8/1985 | Stednitz |
| 4,730,969 | A | 3/1988 | Dohi |
| 5,273,380 | A | 12/1993 | Musacchia |
| 5,334,204 | A | 8/1994 | Clewett et al. |
| 7,819,905 | B2 * | 10/2010 | Newcomb .......... A61B 17/8625 606/311 |
| 9,227,253 | B1 | 1/2016 | Swift et al. |
| 2004/0096293 | A1 | 5/2004 | Tadich |
| 2009/0214321 | A1 | 8/2009 | Wang et al. |
| 2014/0005728 | A1 | 1/2014 | Koay et al. |
| 2014/0257413 | A1 * | 9/2014 | Appenzeller ........ A61B 17/866 606/86 R |

FOREIGN PATENT DOCUMENTS

| | | |
|---|---|---|
| EP | 2092995 A2 | 8/2009 |
| JP | 61-282614 A | 12/1986 |
| JP | 05-012730 | 2/1993 |
| WO | 2012/068641 A1 | 5/2012 |

OTHER PUBLICATIONS

Synthes CMF MatrixRIB Technique Guide Brochure, 33 pages, Jun. 2010.

U.S. Appl. No. 14/926,153, filed Oct. 29, 2015.

* cited by examiner

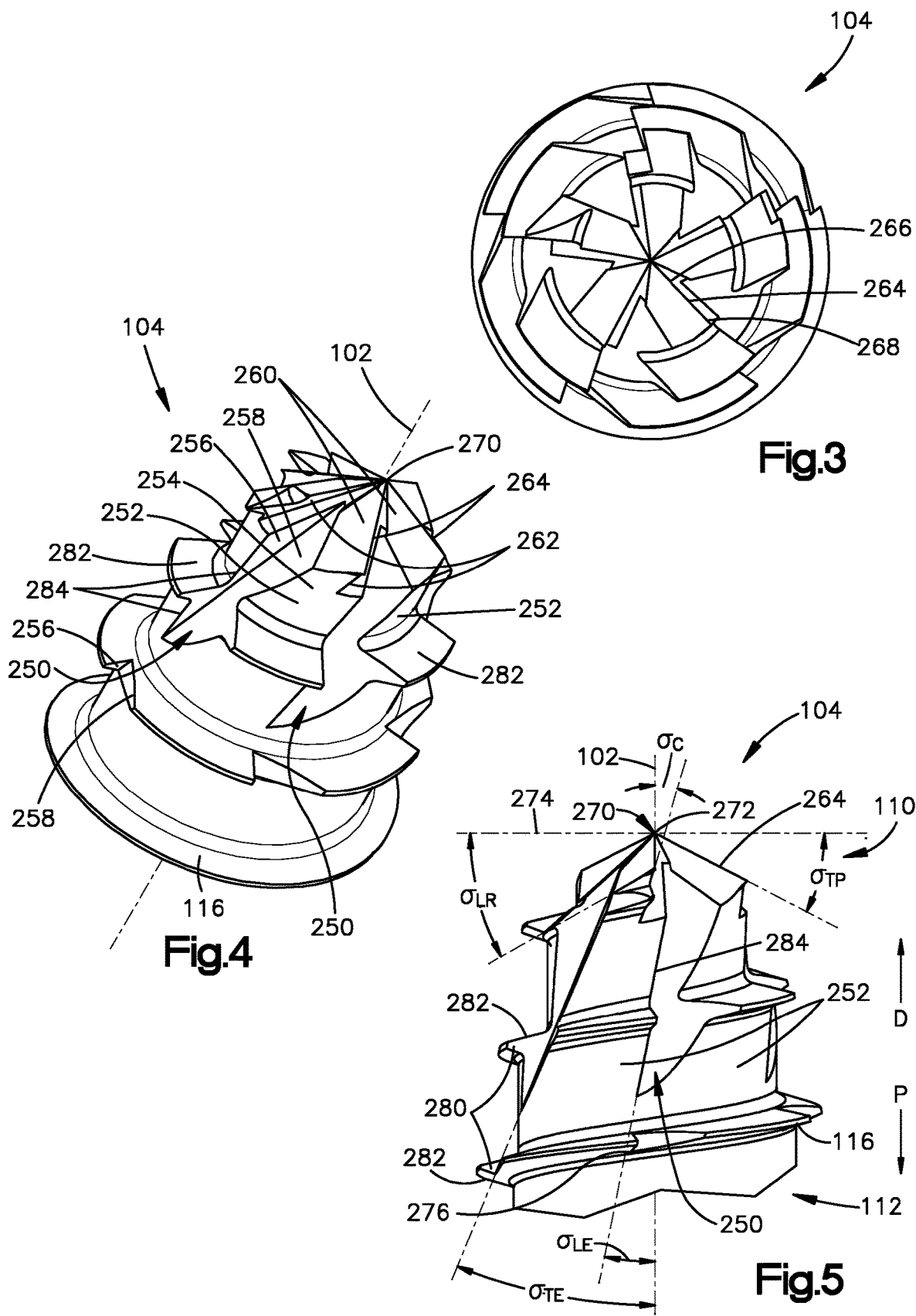

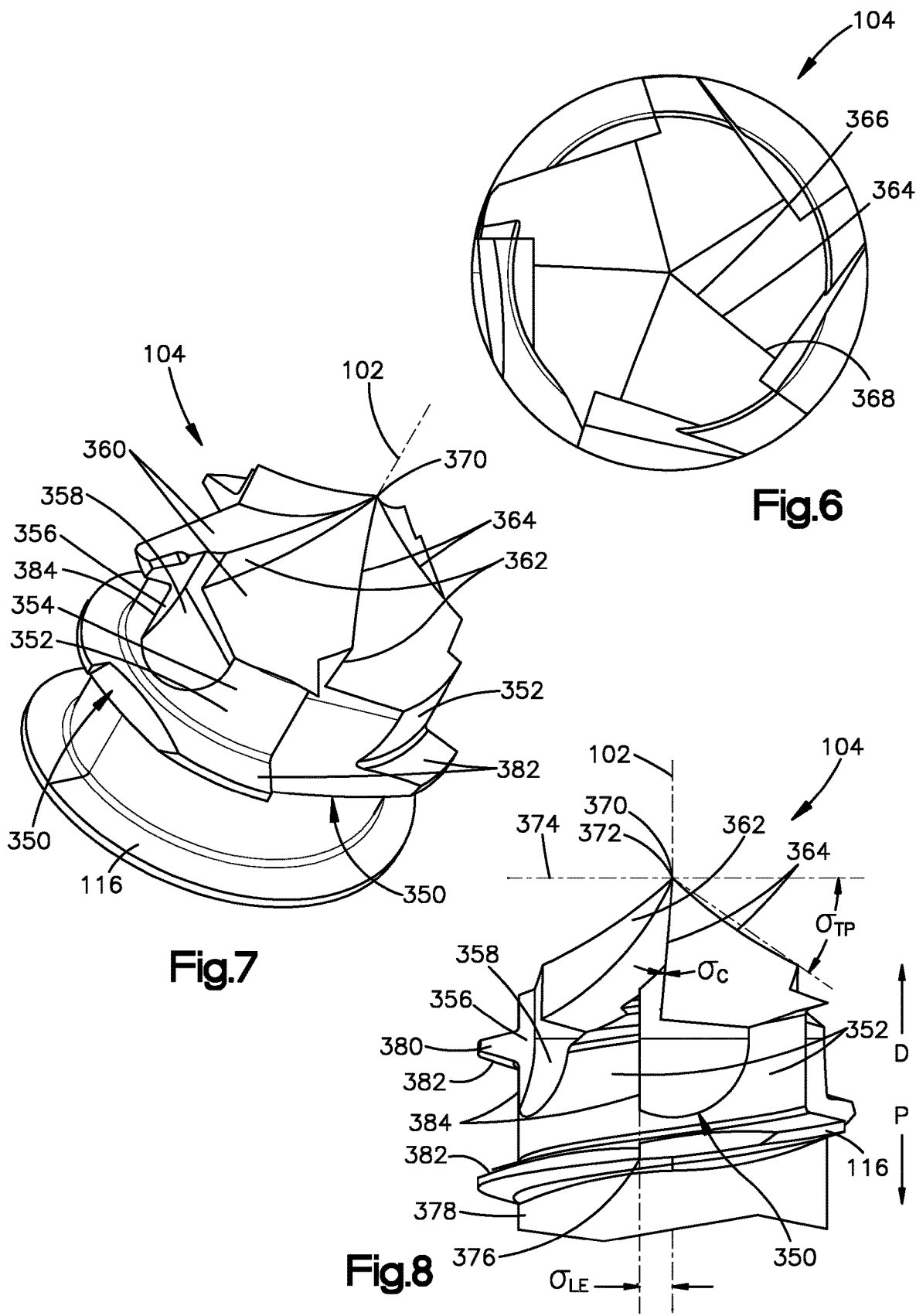

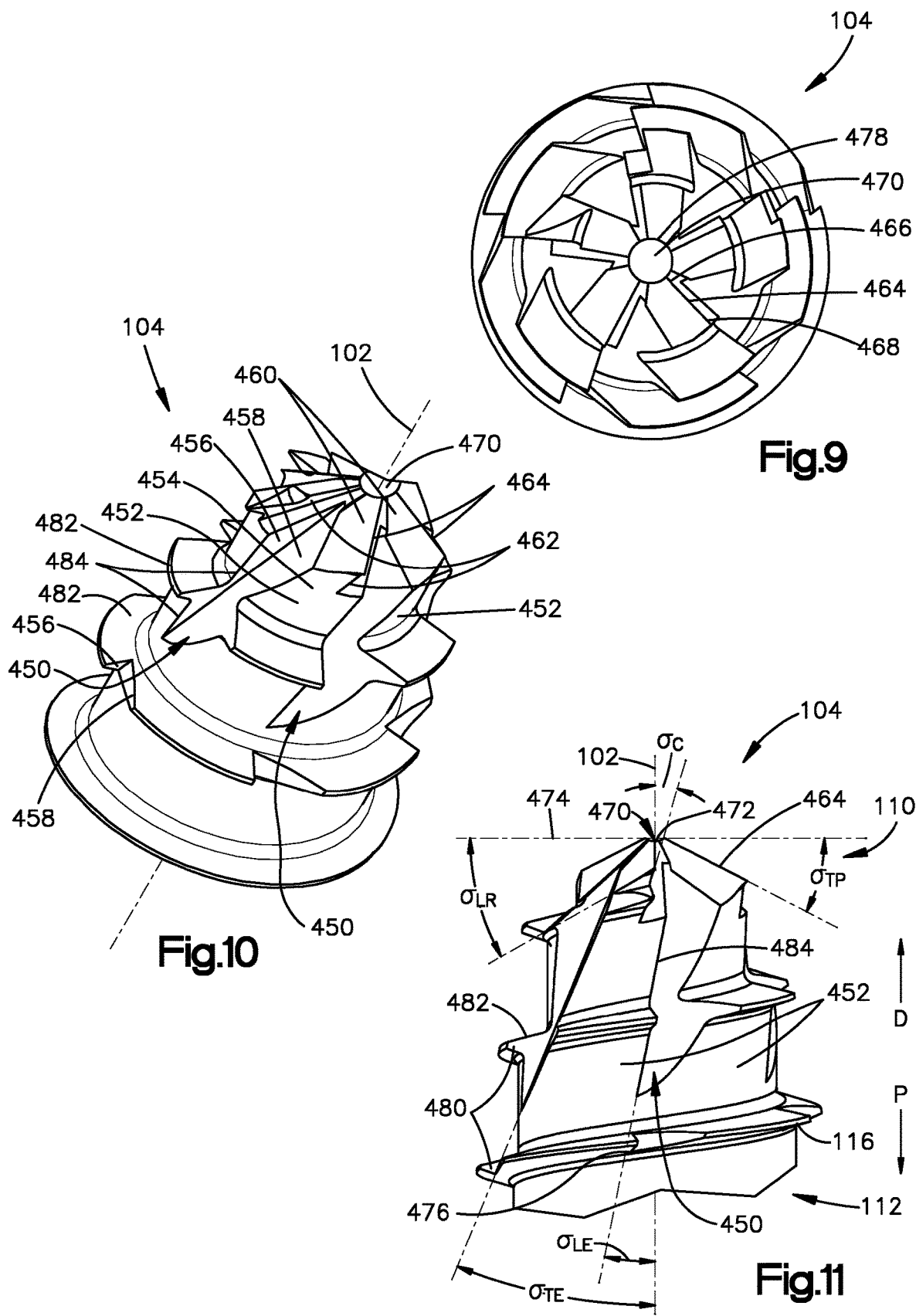

BLUNT TIP BONE SCREW

CROSS-REFERENCE TO RELATED APPLICATIONS

This Application is a divisional of U.S. patent application Ser. No. 14/926,153 filed Oct. 29, 2015, which claims the benefit of U.S. Provisional Application Ser. No. 62/075,021 filed Nov. 4, 2014, the contents of both of which are hereby incorporated by reference as if set forth in their entirety herein.

BACKGROUND

In a surgical rib or sternum fixation, a fixation plate is often secured to a fractured rib or sternum using bone screws. To affix the fixation plate, conventional screws that are either self-tapping or self-drilling have been used. A conventional self-tapping bone screw has a relatively blunt tip that will typically not cause significant damage to soft tissue behind the rib or sternum in the event that the tip penetrates the back side of the rib or sternum. However, conventional self-tapping screws require the use of a drill to prepare a bore hole in the bone for receiving the screw, and the drill can cause soft-tissue wrap, especially when the drill bit penetrates the back side of the rib or sternum. Many self-drilling bone screws have a corkscrew shape with a relatively sharp tip that is capable of penetrating bone. However, if the sharp tip penetrates through the back side of the bone, then the sharp tip can cause damage to the soft tissue behind the bone.

SUMMARY

In at least one embodiment, a bone screw comprises a shaft that has a proximal shaft end and a distal shaft end spaced from the proximal shaft end in a distal direction along a central axis. The shaft is helically threaded between the proximal and distal shaft ends. The bone screw further comprises a tip that extends from the distal shaft end in the distal direction to a tip end. The tip defines one or more lands and at least one cutting flute disposed adjacent the one or more lands, each of the lands having a bore-cutting edge configured to cut a bore into bone. Each bore-cutting edge extends from an inner cutting-edge end to an outer cutting-edge end. The inner cutting-edge end is disposed at a center of the tip end, and the outer cutting-edge end is spaced from the center of the tip end. The bore-cutting edge can define an angle with respect to a plane that is perpendicular to the central axis, the angle in the range of zero to 45 degrees.

In at least another embodiment, a bone screw comprises a shaft that has a proximal shaft end and a distal shaft end spaced from the proximal shaft end in a distal direction along a central axis. The shaft is helically threaded between the proximal and distal shaft ends. The bone screw further comprises a tip that extends from the distal shaft end in the distal direction to a tip end. The tip defines one or more lands and at least one cutting flute disposed adjacent the one or more lands, each of the lands having a bore-cutting edge configured to cut a bore into bone. Each bore-cutting edge extends from an inner cutting-edge end to an outer cutting-edge end. The tip end is solid about the central axis, the inner cutting-edge end is disposed at a center of the tip end, and the outer cutting-edge end is spaced from the center of the tip end.

At least yet another embodiment is a method that comprises abutting a tip of a bone screw against a bone. The tip extends from a shaft of the bone screw in a distal direction to a tip end of the tip, and the tip defines a plurality of lands, each of the lands having a bore-cutting edge. Each bore-cutting edge extends in a radial direction from an inner cutting-edge end disposed at a center of the tip end to an outer cutting-edge end spaced from the center of the tip end. The bone screw is rotated in a first direction of rotation as viewed along the distal direction such that the plurality of cutting edges cut into the bone to form a bore in the bone, the bore having an inner curved surface. Chips cut from the bone are guided away from the tip end in a proximal direction, opposite the distal direction, through cutting flutes formed in the tip between adjacent lands. The bone screw is further rotated in the first direction such that a helical threading disposed on the shaft purchases the inner curved surface of the bore, where the helical threading is disposed on the shaft in the first direction of rotation between a proximal shaft end of the shaft and a distal shaft end of the shaft that is spaced from the proximal shaft end in the distal direction.

BRIEF DESCRIPTION OF THE DRAWINGS

The foregoing summary, as well as the following detailed description of embodiments of the application, will be better understood when read in conjunction with the appended drawings. For the purposes of illustrating the methods and bone screws of the present application, there is shown in the drawings representative embodiments. It should be understood, however, that the application is not limited to the precise methods and bone screws shown. In the drawings:

FIG. 3 shows a top view of one embodiment of the tip of the bone screw of FIGS. 1 and 2;

FIG. 4 shows a perspective view of the tip of FIG. 3;

FIG. 5 shows a side view of the tip of FIG. 3;

FIG. 6 shows a top view of another embodiment of the tip of the bone screw of FIGS. 1 and 2;

FIG. 7 shows a perspective view of the tip of FIG. 6;

FIG. 8 shows a side view of the tip of FIG. 6;

FIG. 9 shows a top view of yet another embodiment of the tip of the bone screw of FIGS. 1 and 2;

FIG. 10 shows a perspective view of the tip of FIG. 9; and

FIG. 11 shows a side view of the tip of FIG. 9.

DETAILED DESCRIPTION

Figure 2:
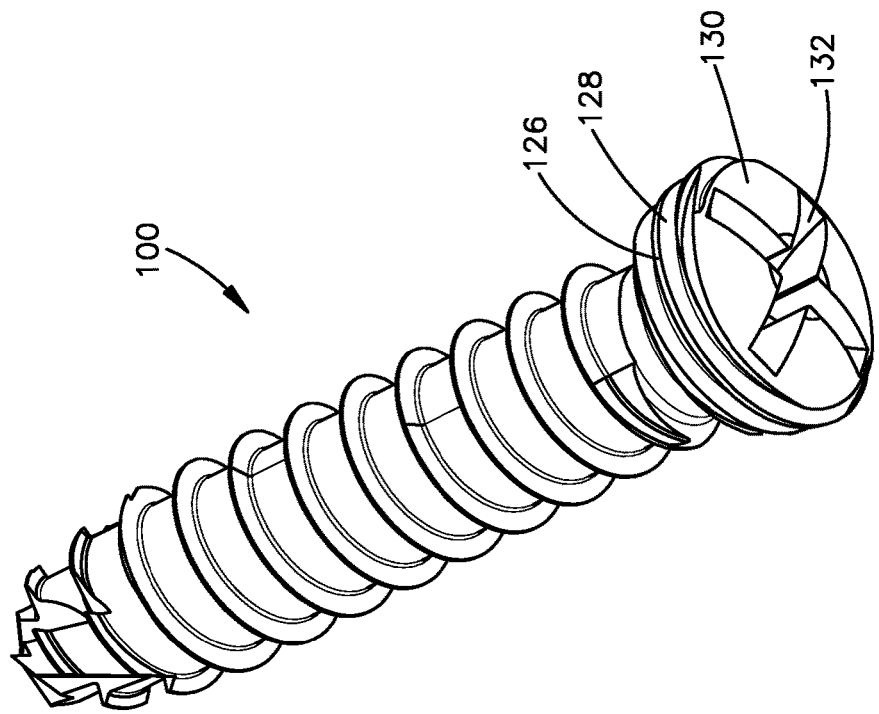
FIG. 2 shows a perspective view from the head of the bone screw of FIG. 1.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the bone screw and related parts thereof. The terminology includes the above-listed words, derivatives thereof and words of similar import.

Figure 1:
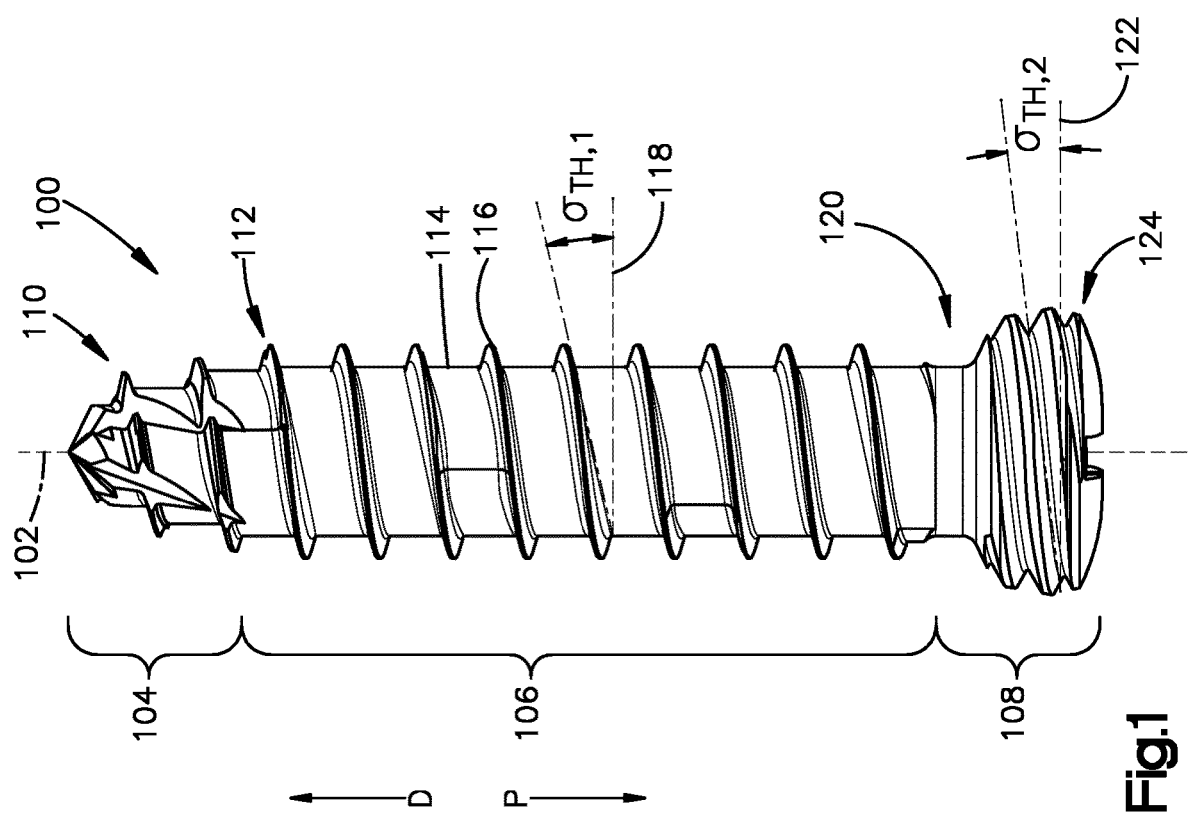
FIG. 1 shows a side view of a bone screw according to one embodiment.

The present disclosure relates to bone screws and methods of using the same. Referring to FIGS. 1 and 2, an embodiment of a bone screw 100 is shown that has a shaft 106 and a tip 104. The bone screw 100 can further have a head 108, although embodiments of the disclosure are not so limited. The shaft 106 has a proximal shaft end 120 and a distal shaft end 112 spaced from the proximal shaft end 120 in a distal direction D along a central axis 102 of the bone screw 100.

The tip 104 (discussed in further detail below) extends from the distal shaft end 112 in the distal direction D to a distal tip end 110, and the head 108 (also discussed in further detail below) extends from the proximal shaft end 120 in a proximal direction P, opposite the distal direction D, to a proximal head end 124.

As will be described in further detail below, the tip 104 includes self-drilling features that enable the bone screw 100 to cut a bore hole into a bone and self-tapping features that enable the bone screw 100 to tap a female thread in the bore hole. Referring briefly to FIGS. 3 to 11, the tip 104 defines one or more lands (e.g., 252, 352, 452) and at least one cutting flute (e.g., 250, 350, 450) disposed adjacent the one or more lands. In at least some embodiments, the tip 104 can define between one and nine lands and between one and nine cutting flutes. Each of the lands has a bore-cutting edge (e.g., 264, 364, 464) configured to cut a bore into bone. Thus, in at least some embodiments, the tip 104 can define between one and nine bore-cutting edges. Each bore-cutting edge has an inner cutting-edge end (e.g., 266, 366, 466) and an outer cutting-edge end (e.g., 268, 368, 468). Each inner cutting-edge end is disposed at a center (e.g., 270, 370, 470) of the tip end, and each outer cutting-edge end is spaced from the center of the tip end.

Referring back to FIGS. 1 and 2, the shaft 106 of the bone screw 100 is substantially cylindrical in shape, although in alternative embodiments, the shaft 106 may taper toward the central axis 102 as it extends from the proximal shaft end 120 toward the tip 104. The shaft 106 has an outer curved surface 114 that extends from the proximal shaft end 120 to the distal shaft end 112. In at least some embodiments, the outer curved surface 114 can be circumferentially solid about the central axis 102 such that the outer curved surface 114 is devoid of openings. Further, in some embodiments, the shaft 106 can be solid about the central axis 102 as the shaft 106 extends from the proximal end 120 to the distal end 112, while in other embodiments the shaft 106 can define at least one bore that extends through the shaft along, for example, the central axis 102.

The shaft 106 includes helical threading 116 that is disposed around the outer curved surface 114 of the shaft 106 between the proximal and distal shaft ends 120 and 112. The threading 116 can be continuous between the proximal and distal shaft ends 120 and 112 such that the threading 116 is devoid of breaks, or can be discontinuous between the proximal and distal shaft ends 120 and 112. The threading 116 can terminate at the proximal shaft end 120 and the distal shaft end 112. Alternatively, the threading 116 can terminate at the outer curved surface 114 before the proximal shaft end 120. The threading 116 defines a thread angle $\theta_{TH,1}$ with respect to a plane 118 that is perpendicular to the central axis 102, where the thread angle $\theta_{TH,1}$ may be a function of the diameter of the screw and the pitch of the threading 116.

The helical threading 116 extends around the shaft 106 such that the bone screw 100 has a rotational purchase direction and a rotational disengagement direction. In this embodiment, the helical threading 116 defines a right-handed thread that extends in a clockwise direction around the shaft 106 from the proximal shaft end 120 toward the distal shaft end 112. As a result, the rotational purchase direction is clockwise as viewed along the distal direction D, and the rotational disengagement direction is counterclockwise as viewed along the distal direction D. In alternative embodiments, however, the helical thread may be a left-handed thread that extends in a counterclockwise direction around the shaft 106 from the proximal shaft end 120 toward the distal shaft end 112 such that the rotational purchase direction is counterclockwise as viewed along the distal direction D, and the rotational disengagement direction is clockwise as viewed along the distal direction D.

The head 108 of the bone screw 100 has a substantially cylindrical shape with a helical thread 126 disposed on the outer curved surface 128 thereof, such that bone screw 100 forms a locking screw. The helical thread 126 is defined by a thread angle $\theta_{TH,2}$ with respect to a plane 122 that is perpendicular to the central axis. The thread angle $\theta_{TH,2}$ may be equal to, or different from, the thread angle $\theta_{TH,1}$ of the helical thread 116. An engagement slot 132 is defined on a proximal surface 130 of the proximal head end 124 for rotatably engaging the bone screw 100 with a drill or screw driver. The slot 132 has a cross-sectional shape, as viewed perpendicularly to the central axis 102, that defines a cross or plus. In alternative embodiments, the head may have any other suitable head configuration either know or not yet discovered. For example, the head (1) may have any other suitable head shape, such as a conical shape or generally spherical shape, (2) may have an engagement feature other than a slot that is a cross or plus, where the engagement feature is suitable for engaging with a drill or screw driver, and/or (3) may be threaded or unthreaded.

Referring to FIGS. 3 to 5, one embodiment of the tip 104 of the bone screw 100 of FIGS. 1 and 2 is shown. The tip 104 is solid about the central axis 102 and has a conical or tapered cylindrical shape defined by one or more, such as five lands 252, positioned circumferentially around the central axis 102. Each land 252 is disposed between a different pair of immediately adjacent cutting flutes 250 formed in the tip 104, where the immediately adjacent cutting flutes 250 are immediately adjacent around the circumference of the tip 104. Thus, each land 252 can be circumferentially spaced from each immediately adjacent land 252 about the central axis 102, and the lands 252 can be sequentially spaced about the central axis 102 at substantially equal rotation angles.

Each land 252 is defined by a plurality of facets and surfaces. For example, each land 252 can include one or more of (i) an outer curved surface 254, (ii) one or more leading-side facets 256, (iii) one or more trailing-side facets 258, (iv) a lip-relief facet 260, and (v) a bore-cutting facet 262. It will be understood that in alternative embodiments, one or more of these surfaces and facets may be omitted, or otherwise configured. In this embodiment, each land 252 has (1) a leading side that is defined by the one or more leading-side facets 256 and the bore-cutting facet 262 of the land 252 and (2) a trailing side that is defined by the one or more trailing-side facets 258 and the lip-relief facet 260 of the land 252. As used herein, the term "leading side" refers to a side that engages the bone when the bone screw is rotated in the rotational purchase direction, while the term "trailing side" refers to a side that follows a corresponding leading side and does not engage the bone when the bone screw is rotated in the rotational purchase direction.

The tip 104 defines one or more, such as five, bone-cutting edges 264, and each bone-cutting edge can be defined by a different land 252. Each bore-cutting facet 262 extends from a corresponding lip-relief facet 260 along a respective one of the bore-cutting edges 264. Each bore-cutting edge 264 extends on a leading side of a corresponding land 252 and cuts into bone abutting the distal tip end 110 when the bone screw 100 is rotated in the rotational purchase direction and advanced in the distal direction D. Each bore-cutting edge 264 includes at an inner cutting-edge end 266 that terminates the bore-cutting edge 264 on one side and an outer cutting-edge end 268 that terminates the bore-cutting edge 264 on the other side. Further, each bore-cutting edge 264 extends from its inner cutting-edge end 266 to its outer cutting-edge end 268 and is straight, although, in alternative embodiments, each bore-cutting edge may be curved in any direction, including a concave or convex direction. Each bore-cutting edge 264 can extend continuously from its inner cutting-edge end 266 to its outer cutting-edge end 268 as shown or can include one or more breaks such that the bore-cutting edge 264 extends discontinuously from its inner cutting-edge end 266 to its outer cutting-edge end 268.

The inner cutting-edge ends 266 of the bore-cutting edges 264 originate from a common center. In this embodiment, the common center is defined by a point 270 of the tip 104 that is co-located with the central axis 102, although embodiments of the disclosure are not so limited. Further, each bore-cutting edge 264 extends radially out from the point 270 and along the proximal direction P to a corresponding outer cutting-edge end 268. As used herein, the term "common center" refers to a central portion of the distal tip end 110 about the central axis 102 that is defined by structure positioned on distal tip end 110, and is not limited to the common center being defined by a point. For example, in alternative embodiments, the common center may be defined by structure other than a point, such as a line, a curved surface, or even an edge defining a closed shape such as a circle, where the edge defines the absence of structure, such as a hole centered about the central axis. Accordingly, in alternative embodiments, each inner cutting-edge end may extend from a central portion of the distal tip end 110 that is not a point.

Referring back to FIG. 5, each bore-cutting edge 264 defines a tip angle $\theta_{TP}$ with respect to a plane 274 that is perpendicular to the central axis 102. The tip angle $\theta_{TP}$ may define, at least in part, how sharp or how blunt the tip end 110 of the tip 104 feels. A smaller tip angle $\theta_{TP}$ defines a tip end 110 that may feel blunter than a larger tip angle $\theta_{TP}$. The tip angle $\theta_{TP}$ may be selected such that the tip end 110 has a relatively bunt feel so as to limit any damage that the tip end 110 might inflict on soft tissue in the event that the tip end 110 penetrates through the back side of the bone. In some embodiments, the blunt tip may be defined by a tip angle $\theta_{TP}$ that ranges from zero degrees to about 45 degrees, and in at least some such embodiments, the blunt tip may be defined by a tip angle $\theta_{TP}$ that ranges from about 15 degrees to about 30 degrees or about 25 degrees to about 30 degrees.

In addition to, or alternatively to, the tip angle $\theta_{TP}$, the number of bore-cutting edges 264, and the length of the bore cutting edges 264 may define, at least in part, how sharp or how blunt the tip end 110 of the tip 104 feels. The bore-cutting edges 264 define a contact surface area that contacts the bone, and in general, a larger contact surface area may have a blunter feel than a smaller contact surface area. Thus, a tip end having a larger number of bore-cutting edges, and hence a larger contact surface area, may have a blunter feel than a tip end having a smaller number of bore-cutting edges. Further, a tip end having at least one bore-cutting edge may have a blunter feel than a conventional self-drilling bone screw that has a corkscrew shape and ends in a point. It will be recognized that embodiments of the disclosure may have as few as one bore-cutting edge or more than one bore-cutting edge.

Each bore-cutting facet 262 extends on a leading side of a land 252 at a cutting angle $\theta_C$ relative to the central axis 102 such that the corresponding bore-cutting edge 264 is configured to cut into bone when the bone screw 100 is rotated in the rotational purchase direction, in this case, clockwise, and advanced in the distal direction D. The cutting angle $\theta_C$ determines how aggressively the bore-cutting edge 264 cuts into bone. In general, larger cutting angles $\theta_C$ may enable the bone screw 100 to cut more aggressively under the same amount of point pressure than smaller cutting angles $\theta_C$. However, excessively large cutting angles $\theta_C$ may also weaken the bore-cutting edge 264, increasing the likelihood that the bore-cutting edge 264 will chip during use. In at least some embodiments, the bore-cutting edge angle $\theta_C$ may be between, for example, zero degrees and fifteen degrees to support cutting into bone.

Each lip-relief facet 260 extends on a trailing side of a land 252 at a lip-relief angle $\theta_{LR}$ relative to the plane 274. The lip-relief angle $\theta_{LR}$ measures the clearance behind the bore-cutting edge 264. Smaller lip-relief angles $\theta_{LR}$ may result in larger thrust forces, and consequently higher heat generation and increased wear. Excessively large lip-relief angles, on the other hand, may weaken the bore-cutting edge 264, increasing the likelihood that the bore-cutting edge 264 will chip during use. In at least some embodiments, the lip-relief angle $\theta_{LR}$ may range from, for example about the thread angle $\theta_{TH,1}$ to about the thread angle $\theta_{TH,1}$ plus ten degrees.

Each cutting flute 250 is a channel or groove formed in the tip 104 that defines an opening in the outer curved surface 254 of the tip 104. Thus, each cutting flute 250 is open at the outer curved surface 254. Each cutting flute 250 is defined by (i) at least one of a leading-side facet 256 and a cutting facet 262 of a land 252 on one side and (ii) at least one of a trailing-side facet 258 and a lip-relief facet 260 of an adjacent land 252 on the other side. Further, each cutting flute 250 has a distal flute end 272 and a proximal flute end 276 that is spaced from the distal flute end 272 with respect to the proximal direction P and that that terminates on the outer curved surface 254 of the tip 104. The proximal flute end 276 can also be angularly offset from the distal flute end 272 with respect to a counterclockwise direction as viewed in the distal direction D, although in alternative embodiments, the proximal flute end 276 can be angularly aligned with the distal flute end 272 or can be angularly offset with respect to a clockwise direction as viewed in the distal direction D (e.g., when the rotational purchase direction is reversed). Each cutting flute 250 is elongate in the proximal direction P from the distal flute end 272 to the proximal flute end 276, and in the distal direction D from the proximal flute end 276 to the distal flute end 272.

In this embodiment, the distal flute ends 272 are co-located with the common center, which in this embodiment is the point 270; however, embodiments of the disclosure are not so limited. Each leading-side facet 256 defines an outer-most edge 284 and extends at a leading-edge angle $\theta_{LE}$ with respect to the central axis 102, and each trailing-side facet 258 extends at a trailing-edge angle $\theta_{LE}$ with respect to the central axis 102. In at least some embodiments, the leading-edge angle $\theta_{LE}$ may be equal to the cutting angle $\theta_C$, and in at least some such embodiments, each leading-side facet 256 may be co-planer with a corresponding bore-cutting facet 262, rather than offset as shown in FIGS. 3 to 5. Further, in some embodiments, each trailing-side facet 258 may be co-planer with a corresponding lip-relief facet 260.

The helical thread 116 extends from the distal shaft end 112 in the distal direction D toward the tip end 110 of the tip 104 at the thread angle $\theta_{TH,1}$. The helical thread 116 is disposed on the outer curved surface 254 of the lands 252 but is fragmented by the cutting flutes 250 to define fragmented segments 282 of the thread 116. Each fragmented segment 282 includes a leading side and a trailing side. The leading side defines a thread-cutting surface 280 that supports thread cutting by the edge 284. Each thread-cutting surface 280 lies on a leading-side facet 256 of a corresponding land 252 and is exposed to a corresponding cutting flute 250. As the bone screw 100 is turned in the rotational purchase direction and advanced into the bone in the distal direction D, the bone-cutting edges 264 form the bore in the bone, and the thread-cutting surfaces 280 cut the thread into the inner curved surface of the bore.

In addition to thread cutting, the tip 104 is configured to support bore forming and thread forming. To support bore forming and thread forming, the outer curved surface 254 of the tip 104 tapers away from the central axis 102 as the tip 104 extends from the tip end 110 toward the distal shaft end 112. Thus, the diameters of the tip 104 and helical thread 116 increase in the proximal direction P from the distal tip end 110 toward the distal shaft end 112. In other words, the tip 104 defines a plurality of cross-sections from the distal tip end 110 to the distal shaft end 112, where each cross-section is in a plane that is perpendicular to the central axis 102 and the diameters of the planes increase from the distal tip end 110 to the distal shaft end 112. This increase in tip and thread diameter deforms the bone to the shape of the tip 104 and the helical thread 116 as the bone screw 100 bores into the bone as discussed further below. In alternative embodiments, however, the tip may not taper, and accordingly, may not support bore forming or thread forming.

Referring to FIGS. 6 to 8, another embodiment of the tip 104 of the bone screw of FIGS. 1 and 2 is shown. The tip 104 extends from the distal shaft end 112 in the distal direction D to a distal tip end 110. Similar to the embodiment of FIGS. 3 to 5, the tip 104 is solid about the central axis 102 and has a conical or tapered cylindrical shape defined by one or more, such as five lands 352, positioned circumferentially around the central axis 102. Each land 352 is disposed between a different pair of immediately adjacent cutting flutes 350 formed in the tip 104, where the immediately adjacent cutting flutes 350 are immediately adjacent with respect to rotation around the circumference of the tip 104. Thus, each land 352 can be circumferentially spaced from each immediately adjacent land 352 about the central axis 102, and the lands 352 can be sequentially spaced about the central axis 102 at substantially equal rotation angles.

Each land 352 is defined by a plurality of facets and surfaces. For example, each land can include one or more of (i) an outer curved surface 354, (ii) one or more leading-side facets 356, (iii) one or more trailing-side facets 358, (iv) a lip-relief facet 360, and (v) a bore-cutting facet 362. It will be understood that in alternative embodiments, one or more of these surfaces and facets may be omitted, or otherwise configured. In this embodiment, each land 352 has (1) a leading side that is defined by the one or more leading-side facets 356 and the bore-cutting facet 362 of the land 352 and (2) a trailing side that is defined by the one or more trailing-side facets 358 and the lip-relief facet 360 of the land 352.

The tip 104 defines one or more, such as five, bone-cutting edges 364, and each bore-cutting edge 364 can be defined by a different land 352. Each bore-cutting facet 362 extends from a corresponding lip-relief facet 360 along a respective one of the bore-cutting edges 364. Each bore-cutting edge 364 extends on a leading side of a corresponding land 352 and cuts into bone abutting the distal tip end 110 when the bone screw is rotated in the rotational purchase direction and advanced in the distal direction D. Each bore-cutting edge 364 includes at an inner cutting-edge end 366 that terminates the bore-cutting edge 364 on one side and an outer cutting-edge end 368 that terminates the bore-cutting edge 364 on the other side. Further, each bore-cutting edge 364 extends from its inner cutting-edge end 366 to its outer cutting-edge end 368. For instance, each bore-cutting edge 364 can extend continuously from its inner cutting-edge end 366 to its outer cutting-edge end 368 as shown or can include one or more breaks such that the bore-cutting edge 364 extends discontinuously from its inner cutting-edge end 366 to its outer cutting-edge end 368.

The inner cutting-edge ends 366 of the bore-cutting edges 364 originate from a common center. In this embodiment, the common center is defined by a point 370 of the tip 104 that is co-located with the central axis 102, although embodiments of the disclosure are not so limited. Further, each bore-cutting edge 364 extends radially out from the point 370 and along the proximal direction P to a corresponding outer cutting-edge end 368 that terminates on the curved outer surface 354.

As best shown in FIG. 8, the bore-cutting edges 364 define a tip angle $\theta_{TP}$ with respect to a plane 374 that is perpendicular to the central axis 102. The tip angle $\theta_{TP}$ may be selected such that the tip end 110 has a relatively bunt feel so as to limit any damage that the tip end 110 might inflict on soft tissue in the event that the tip end 110 penetrates through the back side of the bone. As described above, the tip angle $\theta_{TP}$, the number of bore-cutting edges 264, and the length of the bore cutting edges 264 may define, at least in part, how sharp or how blunt the tip end 110 of the tip 104 feels. A smaller tip angle $\theta_{TP}$ defines a tip end 110 that may feel blunter than a larger tip angle $\theta_{TP}$. Further, a tip end having a larger number of bore-cutting edges, and hence a larger contact surface area, may have a blunter feel than a tip end having a smaller number of bore-cutting edges. It will be recognized that embodiments of the disclosure may have as few as one bore-cutting edge or more than one bore-cutting edge.

Each bore-cutting edge 364 has a concave curvature with respect to the proximal direction, although, in alternative embodiments, each bore-cutting edge may curve in any direction (e.g., in a convex direction) or may be straight. Each bore-cutting facet 362 extends on a leading side of a land 352 at a cutting angle $\theta_C$ (measured as shown in FIG. 5) relative to the central axis 102 such that the corresponding bore-cutting edge 364 is configured to cut into bone when the bone screw is rotated in the rotational purchase direction, in this case, clockwise, and advanced in the distal direction D. In this embodiment, the cutting angle $\theta_C$ is substantially equal to zero degrees (i.e., each bore-cutting edge 364 is aligned with the central axis 102), although, in alternative embodiments, the cutting angle $\theta_C$ may be greater than zero degrees.

Each lip-relief facet 360 extends on a trailing side of a land 352 at varying lip-relief angles $\theta_{LR}$ relative to the plane 374 and provides a clearance for the bone screw to purchase the bone. The lip-relief angles $\theta_{LR}$ vary between the inner cutting-edge end 366 and the outer cutting-edge end 368. In this embodiment, each lip-relief facet 360 has a concave curvature, although, in alternative embodiments, each lip-relief facet 360 may be planar or have a convex curvature. The lip-relief angle $\theta_{LR}$ measures the clearance behind the bore-cutting edge 364. Smaller lip-relief angles $\theta_{LR}$ may result in larger thrust forces, and consequently higher heat generation and increased wear. Excessively large lip-relief angles, on the other hand, may weaken the bore-cutting edge 364, increasing the likelihood that the bore-cutting edge 364 will chip during use.

Each cutting flute 350 is a channel or groove formed in the tip 104 that defines an opening in the outer curved surface 354 of the tip 104. Thus, each cutting flute 350 is open at the outer curved surface 254. Each cutting flute 350 is defined by (i) at least one of a leading-side facet 356 and a cutting facet 362 of a land 352 on one side and (ii) at least one of a trailing-side facet 358 and a lip-relief facet 360 of an adjacent land 352 on the other side. Further, each cutting flute 350 has a distal flute end 372 and a proximal flute end 376 that is spaced from the distal flute end 372 with respect to the proximal direction P and that that terminates on the outer curved surface 354 of the tip 104. The proximal flute end 376 can also be angularly offset from the distal flute end 372 with respect to a counterclockwise direction as viewed in the distal direction D, although in alternative embodiments, the proximal flute end 376 can be angularly aligned with the distal flute end 372 or can be angularly offset with respect to a clockwise direction as viewed in the distal direction D (e.g., when the rotational purchase direction is reversed). Each cutting flute 350 is elongate in the proximal direction P from the distal flute end 372 to the proximal flute end 376. In this embodiment, the distal flute ends 372 are co-located with a common center, which in this embodiment is a point 370; however, embodiments of the disclosure are not so limited.

Each leading-side facet 356 extends at a leading-edge angle $\theta_{LE}$ (measured as shown in FIG. 5) with respect to the central axis 102, and defines an outer-most edge 384. Each trailing-side facet 358 extends substantially parallel to the central axis 102. In this embodiment, the leading-edge angle $\theta_{LE}$ is substantially equal to zero degrees and thus substantially parallel to the central axis 102, although in alternative embodiments, the leading-edge angle $\theta_{LE}$ may be greater than zero degrees. Further, in this embodiment, the leading-side facet 356, and hence the edge 384, is offset from the bore-cutting facet 362 with respect to the counterclockwise direction as viewed in the distal direction D, although in alternative embodiments, the edge 392 can be angularly aligned with the bore-cutting facet 362.

The helical thread 116 extends from a distal end of the shaft of the bone screw in the distal direction D toward the tip end 110 of the tip 104. The helical thread 116 is disposed on the outer curved surface 354 of the lands 352 but is fragmented by the cutting flutes 350 to define fragmented segments 382 of the thread 116. Each fragmented segment 382 includes a leading side and a trailing side. The leading side defines a thread-cutting surface 380 that supports thread cutting by edge 384. Each thread-cutting surface 380 lies on a leading-side facet 356 of a corresponding land 352 and is exposed to a corresponding cutting flute 350. As the bone screw is turned in the rotational purchase direction and advanced into the bone in the distal direction D, the bone-cutting edges 364 form the bore in the bone, and the thread-cutting surfaces 380 cut the thread into the inner curved surface of the bore.

The outer curved surface 354 of the tip 104 and the outer curved surface 378 of the distal end 112 of the shaft of the bone screw do not taper away from the central axis 102 as the tip 104 extends from the distal tip end 110 toward the distal shaft end 112. As a result, the tip 104 in this embodiment may not support bore forming or thread forming, although alternative embodiments of the disclosure may support bore and thread forming.

Referring to FIGS. 9 to 11, yet another embodiment of a tip 104 of the bone screw 100 of FIGS. 1 and 2 is shown. The tip 104 is configured in a manner similar to that of the tip 104 of FIGS. 3 to 5, with at least one notable exception. In FIGS. 9 to 11, the tip 104 is cannulated such that a bore 470 extends from the distal tip end 110 to the distal shaft end 112 along the central axis 102. The bore 470 can also extend from the distal shaft end 112 up to the head 108 or through the proximal head end 124 of the head 108. Thus, in this embodiment, the distal tip end 110 is not solid about the central axis 102.

The tip 104 extends in the distal direction D from the distal shaft end 112 to a distal tip end 110. Similar to the embodiment of FIGS. 3 to 5, the tip 104 has a conical or tapered cylindrical shape defined by one or more, such as five lands 452 positioned circumferentially around the central axis 102. Each land 452 is disposed between a different pair of immediately adjacent cutting flutes 450 formed in the tip 104, where the immediately adjacent cutting flutes 450 are immediately adjacent with respect to rotation around the circumference of the tip 104. Thus, each land 452 can be circumferentially spaced from each immediately adjacent land 452 about the central axis 102, and the lands 452 can be sequentially spaced about the central axis 102 at substantially equal rotation angles.

Each land 452 is defined by a plurality of facets and surfaces. For example, each land 452 can include one or more of (i) an outer curved surface 454, (ii) one or more leading-side facets 456, (iii) one or more trailing-side facets 458, (iv) a lip-relief facet 460, and (v) a bore-cutting facet 462. It will be understood that in alternative embodiments, one or more of these surfaces and facets may be omitted, or otherwise configured. In this embodiment, each land 452 has (1) a leading side that is defined by the one or more leading-side facets 456 and the bore-cutting facet 462 of the land 452 and (2) a trailing side that is defined by the one or more trailing-side facets 458 and the lip-relief facet 460 of the land 452.

The tip 104 defines one or more, such as five, bone-cutting edges 464, and each bone-cutting edge 464 can be defined by a different land 452. Each bore-cutting facet 462 extends from a corresponding lip-relief facet 460 along a respective one of the bore-cutting edges 464. Each bore-cutting edge 464 extends on a leading side of a corresponding land 452 and cuts into bone abutting the distal tip end 110 when the bone screw 100 is rotated in the rotational purchase direction and advanced in the distal direction D. Each bore-cutting edge 464 includes at an inner cutting-edge end 466 that terminates the bore-cutting edge 464 on one side and an outer cutting-edge end 468 that terminates the bore-cutting edge 464 on the other side. Further, each bore-cutting edge 464 extends from the inner cutting-edge end 466 to the outer cutting-edge end 468 and is straight, although, in alternative embodiments, each bore-cutting edge 464 may be curved in any direction, including a concave or convex direction. Each bore-cutting edge 464 can extend continuously from its inner cutting-edge end 466 to its outer cutting-edge end 468 as shown or can include one or more breaks such that the bore-cutting edge 464 extends discontinuously from its inner cutting-edge end 466 to its outer cutting-edge end 368.

The tip 104 defines an edge 478 that defines a closed shape at the distal tip end 110. The edge 478 is circular in this embodiment, although it may have another suitable shape in other embodiments. The edge 478 defines both an opening of the bore 470 in the distal tip end 110, and a common center of the tip 104. The inner cutting-edge ends 466 of the bore-cutting edges 464 originate from the common center defined by the edge 478, and each bore-cutting edge 464 extends radially out from the edge 478 and along the proximal direction P to a corresponding outer cutting-edge end 468 that terminates on the curved outer surface 454. In alternative embodiments, each bore-cutting edge 464 can extend from the edge 478 in a non-radial direction. For example, each bore-cutting edge 464 can extend in a tangential manner from the edge 478 to the curved outer surface 454.

As best shown in FIG. 11, the bore-cutting edges 464 define a tip angle $\theta_{TP}$ with respect to a plane 474 that is perpendicular to the central axis 102. The tip angle $\theta_{TP}$ may be selected such that the tip end 110 has a relatively bunt feel so as to limit any damage that the tip end 110 might inflict on soft tissue in the event that the tip end 110 penetrates through the back side of the bone. As described above, the tip angle $\theta_{TP}$, the number of bore-cutting edges 464, and the length of the bore cutting edges 464 may define, at least in part, how sharp or how blunt the tip end 110 of the tip 104 feels. A smaller tip angle $\theta_{TP}$ defines a tip end 110 that may feel blunter than a larger tip angle $\theta_{TP}$. Further, a tip end having a larger number of bore-cutting edges, and hence a larger contact surface area, may have a blunter feel than a tip end having a smaller number of bore-cutting edges. It will be recognized that embodiments of the disclosure may have as few as one bore-cutting edge or more than one bore-cutting edge.

Each bore-cutting facet 462 extends on a leading side of a land 452 at a cutting angle $\theta_C$ relative to the central axis 102 such that the corresponding bore-cutting edge 464 is configured to cut into bone when the bone screw is rotated in the rotational purchase direction, in this case, clockwise, and advanced in the distal direction D. As described above, the cutting angle $\theta_C$ determines how aggressively the bore-cutting edge 464 cuts into bone. In general, larger cutting angles $\theta_C$ may enable the bone screw 100 to cut more aggressively under the same amount of point pressure than smaller cutting angles $\theta_C$. However, excessively large cutting angles $\theta_C$ may also weaken the bore-cutting edge 464, increasing the likelihood that the bore-cutting edge 464 will chip during use. In at least some embodiments, the bore-cutting edge angle $\theta_C$ may be between, for example, zero degrees and fifteen degrees to support cutting into bone.

Each lip-relief facet 460 extends on a trailing side of a land 452 at a lip-relief angle $\theta_{LR}$ relative to the plane 474 and provides a clearance for the bone screw to purchase the bone. In this embodiment, each lip-relief facet 460 is planar, although, in alternative embodiments, each lip-relief facet may have a concave or convex curvature. As described above, the lip-relief angle $\theta_{LR}$ measures the clearance behind the bore-cutting edge 464. Smaller lip-relief angles $\theta_{LR}$ may result in larger thrust forces, and consequently higher heat generation and increased wear. Excessively large lip-relief angles, on the other hand, may weaken the bore-cutting edge 464, increasing the likelihood that the bore-cutting edge 464 will chip during use. In at least some embodiments, the lip-relief angle $\theta_{LR}$ may range from, for example about the thread angle $\theta_{TH,1}$ to about the thread angle $\theta_{TH,1}$ plus ten degrees.

Each cutting flute 450 is a channel or groove formed in the tip 104 that defines an opening in the outer curved surface 454 of the tip 104. Thus, each cutting flute 450 is open at the outer curved surface 454. Each cutting flute 450 is defined by (i) at least one of a leading-side facet 456 and a cutting facet 462 of a land 452 on one side and (ii) at least one of a trailing-side facet 458 and a lip-relief facet 460 of an adjacent land 452 on the other side. Further, each cutting flute 450 has a distal flute end 472 that originates at edge 478 and a proximal flute end 476 that is spaced from the distal flute end 472 with respect to the proximal direction P and that that terminates on the outer curved surface 454 of the tip 104. The proximal flute end 476 can also be angularly offset from the distal flute end 472 with respect to a counterclockwise direction as viewed in the distal direction D, although in alternative embodiments, the proximal flute end 476 can be angularly aligned with the distal flute end 472 or can be angularly offset with respect to a clockwise direction as viewed in the distal direction D (e.g., when the rotational purchase direction is reversed). Each cutting flute 450 is elongate in the proximal direction P from the distal flute end 472 to the proximal flute end 476.

In this embodiment, the distal flute ends 472 are co-located with a common center, which in this embodiment is the edge 478; however, embodiments of the disclosure are not so limited. Each leading-side facet 456 defines an outer-most edge 484 and extends at a leading-edge angle $\theta_{LE}$ with respect to the central axis 102, and each trailing-side facet 458 extends at a trailing-edge angle $\theta_{TE}$ with respect to the central axis 102. In at least some embodiments, the leading-edge angle $\theta_{LE}$ may be equal to the cutting angle $\theta_C$, and in at least some such embodiments, each leading-side facet 456 may be co-planer with a corresponding bore-cutting facet 462, rather than offset as shown in FIGS. 9 to 11. Further, in some embodiments, each trailing-side facet 458 may be co-planer with a corresponding lip-relief facet 460. Thus, in some embodiments, the trailing-edge angle $\theta_{TE}$ can be equal to a difference between 90 degrees and the lip relief angle $\theta_{TE}$ due to the trailing-edge angle θm and the lip relief angle $\theta_{TE}$ being defined relative to references 474 and 102, respectively, that are perpendicular to one another.

The helical thread 116 extends from a distal shaft end 112 in the distal direction D toward the tip end of the tip 104 at the thread angle $\theta_{TH,1}$. The helical thread 116 is disposed on the outer curved surface 454 of the lands 452 but is fragmented by the cutting flutes 450 to define fragmented segments 482 of the thread 116. Each fragmented segment 482 includes a leading side and a trailing side. The leading side defines a thread-cutting surface 480 that supports thread cutting by the edge 484. Each thread-cutting surface 480 lies on a leading-side facet 456 of a corresponding land 452 and is exposed to a corresponding cutting flute 450. As the bone screw is turned in the rotational purchase direction and advanced into the bone in the distal direction D, and bone-cutting edges 464 form the bore in the bone, and the thread-cutting surfaces 480 cut the thread into the inner curved surface of the bore.

The outer curved surface 454 of the tip 104 tapers away from the central axis 102 as the tip 104 extends from the tip end 110 toward the distal shaft end 112. Thus, the diameters of the tip 104 and helical thread 116 increase in the proximal direction P from the distal tip end 110 toward the distal shaft end 112. In other words, the tip 104 defines a plurality of cross-sections from the distal tip end 110 to the distal shaft end 112, where each cross-section is in a plane that is perpendicular to the central axis 102 and the diameters of the planes increase from the distal tip end 110 to the distal shaft end 112. Thus, the tip 104 can supports bore forming and thread forming as described above in relation to the embodiment of FIGS. 3 to 5.

Referring now to FIGS. 1 to 11, during insertion of the bone screw 100, a tip of a screw driver or drill (not shown) is engaged with the slot 132 of the head 108 of the bone screw 100. The distal tip end 110 of the tip 104 of the bone screw 100 can be passed through a corresponding bore in a fixation plate (if a fixation plate is used) and is pressed against the bone. The bone screw 100 is then rotated in the rotational purchase direction while a force is applied to the bone screw 100 in the distal direction D. As the bone screw 100 is rotated and advanced in the distal direction D, the distal tip end 110 of the bone screw 100 pierces the bone, and the bore-cutting edges (264, 364, 464) of the bone screw 100 come into contact with the bone. As the bone screw 100 advances into the bone thereby forming a bore, the bore-cutting edges (264, 364, 464) cut chips from the bone, and the bone chips are guided through the cutting flutes (250, 350, 450) in the proximal direction P and away from the bottom of the bore. The surface area of the bone screw 100 that is in contact with the bone increases until each full bore-cutting edge (264, 364, 464) is in contact with the bone. The surface area of the bore-cutting edges (264, 364, 464) enables the tip end 110 of the bone screw 100 to have a blunter feel than the tip of a conventional self-drilling bone screw that has a corkscrew shape and terminates at a single point.

When the outer cutting-edge ends (268, 368, 468) of the bore-cutting edges (264, 364, 464) come into contact with the bone, the thread-cutting surfaces (280, 380, 480) on the one or more leading-side facets (256, 356, 456) of the lands (252, 352, 452) begin cutting away chips of bone from the inner curved surface of the bore to define a female thread in the bore of the bone. These chips are also guided through the cutting flutes (250, 350, 450) in the proximal direction P and away from the bottom of the bore in the bone. Rotation of the bone screw 100 continues as (1) the helical thread 116 engages the female thread formed in the bone and (2) the helical thread 136 (if employed) of the head 108 engages a corresponding female thread formed in the bore on the fixation plate (if employed), thereby locking the bone screw 100 to the fixation plate. In the event that the bone screw 100 pierces through the back side of the bone, the tip 104 may limit damage to soft tissue behind the bone, compared to conventional self-tapping screws.

In embodiments where the tip 104 is tapered such as the embodiments in FIGS. 3 to 5 and 9 to 11, as the bone screw 100 advances into the bone, the increasingly larger-diameter portions of the tapered tip 104 enter the bore in the bone. The curved outer surface (254, 454) at the increasingly larger-diameter portions of the tip 104 bears against the inner curved surface of the bore in the bone, thereby deflecting the inner curved surface of the bore radially outward to enlarge the bore. Further, the fragmented segments (282, 482) of the helical thread 116 on the increasingly larger-diameter portions of the tip 104 deform the female thread cut into in the bone by the thread-cutting surfaces (280, 480) to enlarge the diameter of the female thread.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure. Further, it should be appreciated, that the term substantially indicates that certain directional components are not absolutely perpendicular to each other and that substantially perpendicular means that the direction has a primary directional component that is perpendicular to another direction.

What is claimed is:

1. A method of fixing a bone screw to bone, the bone screw having a shaft and a tip that extends from the shaft in a distal direction along a central axis to a tip end, the method comprising:
    abutting the tip against a bone, wherein the tip defines a plurality of lands and a plurality of cutting flutes, each cutting flute disposed between a different pair of the lands, each of the lands defined by a leading side and a trailing side with respect to a first direction of rotation about the central axis, each leading side having a bore-cutting edge that defines a tip angle with respect to a plane that is perpendicular to the central axis, the tip angle in a range of 15 degrees to 30 degrees;
    rotating the bone screw in the first direction of rotation about the central axis, wherein 1) each bore-cutting edge cuts into the bone to form a bore in the bone, such that the bore has a curved inner surface, and 2) helical threading of the shaft purchases in the curved inner surface of the bore, the helical threading extending in the first direction of rotation as viewed along the distal direction; and
    during the rotating step, guiding chips cut from the bone away from the tip end in a proximal direction through the cutting flutes of the tip, wherein the proximal direction is opposite the distal direction.

2. The method of claim 1, wherein during the rotating step, a thread-cutting surface of at least one leading side cuts threading into the curved inner surface of the bone such that the helical threading of the shaft purchases with the threading of the curved inner surface.

3. The method of claim 2, wherein each leading side comprises a thread-cutting surface that cuts the threading into the curved inner surface of the bone.

4. The method of claim 1, wherein the shaft has a proximal shaft end and a distal shaft end spaced from the proximal shaft end in the distal direction, wherein the helical threading of the shaft is between the proximal and distal shaft ends, wherein the tip extends from the distal shaft end in the distal direction to a tip end, and wherein each bore-cutting edge extends from an inner cutting-edge end, disposed at a center of the tip end, to an outer cutting-edge end that is spaced from the center of the tip end.

5. The method of claim 4, wherein each bore-cutting edge extends in a radial direction relative to the central axis from the inner cutting-edge end to the outer cutting-edge end.

6. The method of claim 1, wherein:
    each bore-cutting edge is defined at the leading side of a corresponding land.

7. The method of claim 1, wherein the tip defines at least three bore-cutting edges.

8. The method of claim 1, wherein a center of the tip end is solid about the central axis and defined by a single point.

9. The method of claim 1, wherein:
    each land of the plurality of lands includes a lip-relief facet that extends from the bore-cutting edge of the land along the bore-cutting edge of the land, wherein as the bore-cutting edge cuts into the bone the lip-relief facet provides clearance behind the bore-cutting edge.

10. The method of claim 1, wherein an outer curved surface of the tip is tapered from the shaft toward the tip end.

11. The method of claim 1, wherein the tip end is cannulated so as to define a hole about the central axis of the tip end.

12. The method of claim 1, wherein each land includes a bore cutting facet that extends on a leading side of the land at a cutting angle relative to the central axis, and the cutting angle is in a range between 0 degrees and fifteen degrees.

13. A method of fixing a bone screw to bone, the bone screw having a shaft and a tip that extends from the shaft in a distal direction along a central axis to a tip end that is solid about the central axis and defines a single point, the method comprising:
- abutting the tip against a bone, wherein the tip defines a plurality of lands and a plurality of cutting flutes, each cutting flute disposed between a different pair of the lands, each of the lands having a bore-cutting edge configured to cut a bore into bone and an outer surface, and wherein the bore-cutting edge of each respective land of the plurality of lands extends radially out from an inner cutting-edge end that is disposed at the single point to an outer cutting-edge end that is spaced from the center of the tip end and that terminates on the outer surface of the respective land, and wherein each bore-cutting edge defines a tip angle with respect to a plane that is perpendicular to the central axis, the tip angle in a range of 15 to 30 degrees;
- rotating the bone screw in a first direction of rotation about the central axis, wherein 1) each bore-cutting edge cuts into the bone to form a bore in the bone, such that the bore has a curved inner surface, and 2) helical threading of the shaft purchases in the curved inner surface of the bore, the helical threading extending in the first direction of rotation as viewed along the distal direction; and
- during the rotating step, guiding chips cut from the bone away from the tip end in a proximal direction through the cutting flutes of the tip, wherein the proximal direction is opposite the distal direction.

14. The method of claim 13, wherein during the rotating step, at least one thread-cutting surface of the shaft cuts threading into the curved inner surface of the bore such that the helical threading of the shaft purchases with the threading of the curved inner surface.

15. The method of claim 14, wherein:
- each land is defined by a leading side and a trailing side with respect to the first direction of rotation; and
- each leading side includes a thread-cutting surface configured to cut threading into the bone, and wherein during the rotating step, each thread-cutting surface cuts the threading into the curved inner surface of the bone.

16. The method of claim 13, wherein the shaft has a proximal shaft end and a distal shaft end spaced from the proximal shaft end in the distal direction, wherein the helically threading of the shaft is between the proximal and distal shaft ends.

17. The method of claim 13, wherein each bore-cutting edge extends in a radial direction relative to the central axis from an inner cutting-edge end to the outer cutting-edge end.

18. The method of claim 13, wherein each of the plurality of cutting flutes has a proximal flute end and a distal flute end spaced from the proximal flute end with respect to the distal direction and the distal flute end is co-located with the single point of the tip end.

19. The method of claim 13, wherein:
- each land is defined by a leading side and a trailing side with respect to the first direction of rotation; and
- each bore-cutting edge is defined at the leading side of a corresponding land.

20. The method of claim 13, wherein each land includes a bore-cutting facet and a lip-relief facet that extends from the bore-cutting facet along the bore-cutting edge of the land, wherein as the bore-cutting edge cuts into bone the lip-relief facet provides clearance behind the bore-cutting edge.

21. The method of claim 13, wherein the tip includes a helical thread that extends around the tip in the first direction of rotation as viewed along the distal direction and the helical thread is fragmented by the plurality of cutting flutes so as to define fragmented segments of the helical thread.

22. The method of claim 13, wherein an outer curved surface of the tip is tapered from the shaft toward the tip end.

23. The method of claim 13, wherein the point is a geometric point and bore-cutting edges directly meet with one another at the geometric point.

24. The method of claim 13, where the single point is disposed on the central axis.

25. The method of claim 13, wherein each land includes a bore cutting facet that extends on a leading side of the land at a cutting angle relative to the central axis, and the cutting angle is in a range between 0 degrees and fifteen degrees.

* * * * *